United States Patent
Ziskin et al.

(10) Patent No.: US 8,724,872 B1
(45) Date of Patent: May 13, 2014

(54) SINGLE RADIATION DATA FROM MULTIPLE RADIATION SOURCES

(75) Inventors: Vitaliy Ziskin, Brighton, MA (US); Boris Oreper, Chestnut Hill, MA (US)

(73) Assignee: L-3 Communications Security and Detection Systems, Inc., Woburn, MA (US)

(*) Notice: Subject to any disclaimer, the term of this patent is extended or adjusted under 35 U.S.C. 154(b) by 896 days.

(21) Appl. No.: 12/711,893

(22) Filed: Feb. 24, 2010

Related U.S. Application Data

(60) Provisional application No. 61/155,438, filed on Feb. 25, 2009.

(51) Int. Cl.
*G06K 9/00* (2006.01)

(52) U.S. Cl.
USPC .......................................................... 382/131

(58) Field of Classification Search
None
See application file for complete search history.

(56) References Cited

U.S. PATENT DOCUMENTS

| | | | | |
|---|---|---|---|---|
| 5,852,646 A * | 12/1998 | Klotz et al. | | 378/8 |
| 6,421,412 B1 * | 7/2002 | Hsieh et al. | | 378/9 |
| 6,628,745 B1 * | 9/2003 | Annis et al. | | 378/21 |
| 6,873,677 B2 * | 3/2005 | Kaufman | | 378/4 |
| 7,203,269 B2 * | 4/2007 | Huber et al. | | 378/10 |
| 7,218,700 B2 * | 5/2007 | Huber et al. | | 378/10 |
| 7,680,241 B2 * | 3/2010 | David et al. | | 378/7 |
| 7,864,924 B2 * | 1/2011 | Ziskin et al. | | 378/136 |
| 8,106,365 B2 * | 1/2012 | Perticone et al. | | 250/393 |
| 2004/0079232 A1 * | 4/2004 | Groh et al. | | 96/1 |
| 2004/0213371 A1 * | 10/2004 | Bruder et al. | | 378/9 |
| 2009/0122953 A1 * | 5/2009 | Imai | | 378/5 |
| 2010/0092060 A1 * | 4/2010 | Bruder et al. | | 382/131 |
| 2010/0246763 A1 * | 9/2010 | Kang et al. | | 378/57 |
| 2010/0277312 A1 * | 11/2010 | Edic et al. | | 340/540 |
| 2012/0119103 A1 * | 5/2012 | Perticone et al. | | 250/395 |

FOREIGN PATENT DOCUMENTS

EP    1995757 A1 * 11/2008 ............. H01J 35/06

* cited by examiner

*Primary Examiner* — Robert Morgan
*Assistant Examiner* — Michael Tomaszewski
(74) *Attorney, Agent, or Firm* — Fish & Richardson P.C.

(57) ABSTRACT

A signal is reconstructed from multiple radiation sources. Data detected by a detector is accessed. The data includes a combined representation of radiation emitted concurrently from two sources of radiation. A representation of the radiation emitted from one of the two sources of radiation is determined from the data.

19 Claims, 6 Drawing Sheets

US 8,724,872 B1

SINGLE RADIATION DATA FROM MULTIPLE RADIATION SOURCES

CROSS-REFERENCE TO RELATED APPLICATION

This application claims the benefit of U.S. Provisional Application No. 61/155,438, filed Feb. 25, 2009 and titled SINGLE X-RAY DATA FROM MULTIPLE X-RAY SOURCES, which is incorporated by reference in its entirety.

TECHNICAL FIELD

This description relates to producing single radiation data from multiple radiation sources, such as, for example, X-ray data from multiple X-ray sources.

BACKGROUND

Data collected from a single moving beam of radiation that illuminates an object may be used to create an image representing the object.

SUMMARY

Techniques for reconstructing an image of an object scanned concurrently with multiple moving X-ray beams are disclosed. In some systems, a single moving X-ray beam scans an object at varying view angles. The relative position of the X-ray beam and the detector determine the view angle corresponding to a particular position of the X-ray beam. Thus, by moving the single X-ray beam about the object, a number of views of the object at different view angles may be obtained. For each view angle of the X-ray beam, the single X-ray beam impinges on a different portion of the object. The X-ray beam is attenuated as a result of interacting with the material in the object, and a detector detects the attenuated beam and produces signals in response to detecting the attenuated beam. As a result of the single X-ray beam moving about the object, the detector produces signals representing the amount of radiation sensed by the detector for each of the various view angles. The detector signals generated in response to detecting X-ray radiation over the various view angles may be back-projected or otherwise analyzed to produce a computed tomography (CT) image that represents the amount of attenuation as a function of detector location and view angle. This CT image may be transformed into image data that represents the density of the object as a function of space.

In a system employing a single moving X-ray beam, it may be relatively straightforward to determine the view angle because the position of the moving X-ray beam corresponding to the detector data is known. However, applying similar techniques to data collected from a system in which two or more X-ray beams scan the object at the same time may present challenges. In particular, when two or more X-ray beams scan the object at the same time, X-ray radiation reaching the detector may be from any of the two or more X-ray beams. For example, in a system that scans an object with two X-ray beams simultaneously or concurrently, the detector may detect both X-ray beams at the same time. The detector combines the radiation detected from both beams to produce detector signals representing the total amount of radiation detected by the detector. Because each of the two X-ray beams is located at a different position relative to the detector and the object, each of the two X-ray beams have a different view angle. However, because data from both sources is detected simultaneously, there is no known way to separate each component of the detected signal. As a result, application of the CT image techniques discussed above, which rely on knowledge of the position of the X-ray beam relative to the detector, to data from a system in which multiple X-ray beams scan the object at the same time may yield inaccurate and/or unusable results.

In contrast, the techniques discussed below disclose scanning an object with multiple moving X-ray beams concurrently, detecting the concurrently scanned X-ray beams, and analyzing the resulting detector data to determine a representation of the object attributable to only one of the multiple X-ray beams. In this manner, although the object is scanned by multiple X-ray beams at the same time, the detector data may be used to produce data as if only one X-ray beam scanned the object. The produced data may be a single X-ray source sinogram.

In one general aspect, an imaging system includes a first source of radiation configured to direct first radiation towards an object, a second source of radiation configured to direct second radiation towards the object concurrently with the first radiation, and a detector configured to detect the first radiation and the second radiation and to create data including a combination of the first radiation with the second radiation. The system also includes a processor and an electronic storage coupled to the processor. The electronic storage includes instructions that, when executed, cause the processor to receive the data from the detector, and determine, from the data, a representation of the first radiation.

Implementations may include one or more of the following features. The first source of radiation may be an X-ray source and the second source of radiation may be an X-ray source, and the first radiation may be a first X-ray beam and the second radiation may be a second X-ray beam. The first X-ray beam and the second X-ray beam may move concurrently relative to the object. The instructions to determine a representation of the first radiation may include instructions to reconstruct an attenuation of the first X-ray beam caused by the first X-ray beam passing through the object. The instructions to determine a representation of the first radiation may include instructions to determine a location of the first source of radiation relative to the object and a view angle of the first source of radiation relative to the object.

The first X-ray beam and the second X-ray beam may be generated by scanning an electron beam across a target that is configured to emit X-rays in response to interacting with the electron beam, and the first X-ray beam and the second X-ray beam may move with the electron beam. The first X-ray beam source may include a track that includes multiple targets placed along the track, and the second X-ray source may include a track that includes multiple targets placed along the track. The first X-ray beam may be generated by directing the electron beam to one of the multiple targets on the first track, and the second X-ray beam may be generated, concurrently with the first X-ray beam, by steering the electron beam to one of the multiple targets on the second track. The first track may be a different configuration than the second track. The first X-ray source and the second X-ray source may include a portion that does not emit an X-ray beam toward the object. The first radiation and the second radiation may move in a predetermined pattern relative to each other and relative to the object. The first radiation and the second radiation may have a circular motion about the object or an elliptical motion about the object.

In some implementations, the imaging system also may include a display. The instructions may include instructions to produce a visual representation of the first radiation and enable presentation of the visual representation on the display. The data may include a summation of the intensity of the first radiation and the intensity of the second radiation after the first and second radiation interact with the object. The first and second radiation may be scattered from the object, the combination of the first radiation and the second radiation may include a summation of backscatter of the first and second radiation from the object. The determined representation of the first radiation may include an amount of the backscatter attributable to the first radiation scattered from the object. The first and second radiation may pass through the object, the object attenuates the first radiation and the second radiation, and the detector detects the attenuated first radiation and the attenuated second radiation.

In another general aspect, a signal is reconstructed from multiple radiation sources. Data detected by a detector is accessed. The data includes a combined representation of radiation emitted concurrently from two sources of radiation. A representation of the radiation emitted from one of the two sources of radiation is determined from the data.

Implementations may include one or more of the following features. The two sources of radiation may move relative to each other and relative to an object to be scanned in a predetermined pattern. The radiation that is emitted from the two sources may include X-ray radiation. The combined representation may include a summation of the X-ray radiation emitted from the two sources. Determining a representation of the radiation emitted from one of the sources includes determining a position of the one of the sources of radiation relative to a scan region and a view angle of the one of the sources of radiation relative to the scan region may be determined.

In another general implementation, an apparatus for generating multiple moving X-ray spots includes a track that includes multiple emission targets placed along the track. The multiple discrete emission targets are configured to emit X-rays in response to being irradiated with an electron beam. The track also includes multiple discrete blank targets that suppress the emission of X-rays in response to being irradiated with the electron beam. The number of blank targets is proportional to the number of generated moving X-ray spots.

Implementations may include one or more of the following features. The track may be sized to fit into a non-rotating CT. The multiple emission targets may be arranged in a two-dimensional pattern.

In another aspect, a computer-readable medium encoded with a computer program includes instructions that, when executed, operate to cause a computer to perform operations including accessing data detected by a detector, the data including a combined representation of radiation emitted concurrently from two sources of radiation, and determining, from the data, a representation of the radiation emitted from one of the two sources of radiation. In another aspect, two or more X-ray sources move relative to a scanned object and radiation from the two or more X-ray sources simultaneously illuminates the scanned object. One or more detectors sense radiation from the two or more X-ray sources. The radiation sensed from the two or more X-ray sources is combined to produce data that is representative of the radiation as if the radiation had been separately received from the two or more X-ray sources.

Implementations may include one or more of the following features. The X-ray sources may move around the scanned object. The X-ray sources may move with linear motion. The X-ray sources may move with circular or elliptical motion. The X-ray sources may move in one direction or multiple directions. The X-ray sources may move in a first direction and in a second direction opposite to the first direction. The X-ray sources may be generated by a scanning electron beam striking a target configured to emit X-rays in response to interaction with the scanning electron beam. The X-ray sources may be generated by multiple X-ray tubes. The electron current in the X-ray tubes may be configured to be switched between an ON state and an OFF state. The electron current may be turned ON and OFF by actuation of an electron source in the X-ray tube. The electron source may be a field emission cathode. The electron source may be a photocathode. The X-ray sources may include one or more dark portions that do not emit X-rays. The dark portions may be obstructions that block the X-ray radiation prior to the X-ray radiation being sensed by the detectors. The dark portions may include material that does not emit X-rays in response in response to interaction with an electron beam. The dark portions may be portions traversed by the electron beam while the electron beam is turned off.

Implementations of the techniques discussed above may include a method or process, a system or apparatus, or computer software on a computer-accessible medium.

DESCRIPTION OF THE DRAWINGS

Like reference numbers refer to like elements.

DETAILED DESCRIPTION

Figure 1A:
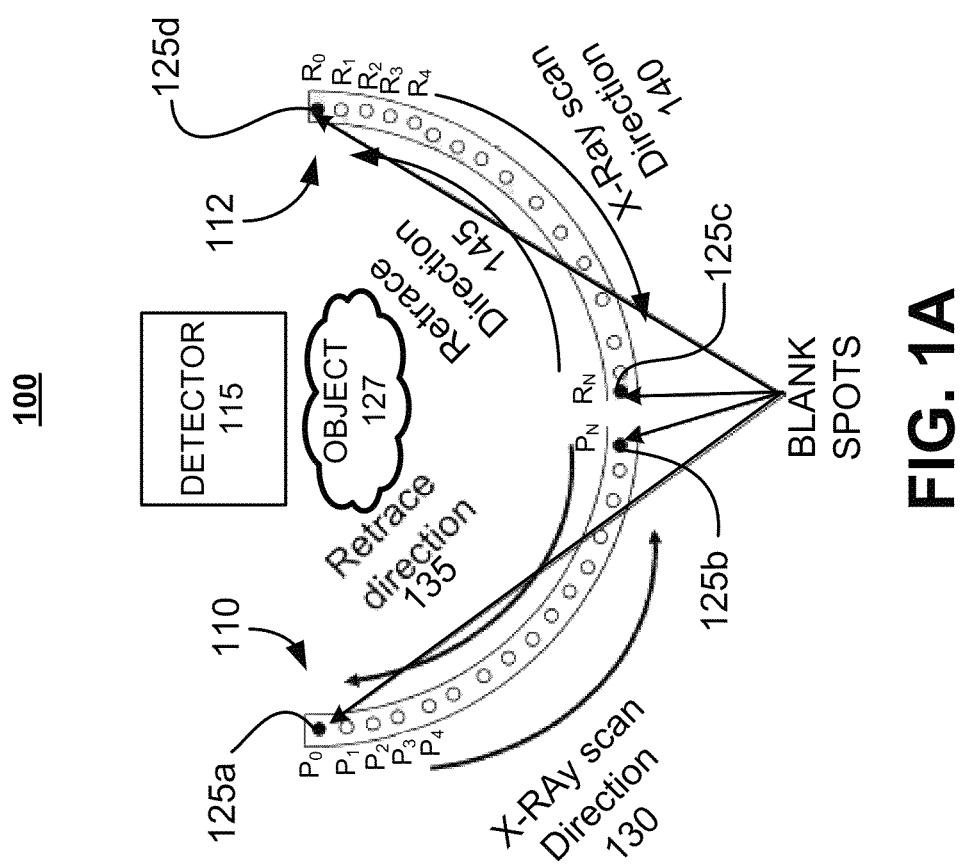
FIG. 1A shows an example system for producing a single X-ray source sinogram from detector data collected from multiple traveling X-ray spots.

Techniques are described for producing a single X-ray source sinogram from detector data collected from multiple X-ray spots that simultaneously illuminate an object to be scanned and imaged. An image of an object that is scanned with multiple X-ray spots at the same time is reconstructed from detector data, which combines radiation from the multiple X-ray spots, as if the object had been scanned with a single X-ray spot. The image may be a sinogram that represents the density of the object and is derived from the scattering data associated with cross-sectional scans at various view points of an object. The multiple X-ray spots may be moving X-ray spots and may be referred to as traveling X-ray spots. The object may be, for example, luggage in a package screener or a portion of a human body, such as an organ. The traveling X-ray spots illuminate the object to be scanned, and the radiation in the traveling X-ray spots is attenuated as the radiation passes through the object. Radiation that passes through the object to be scanned is sensed by a detector. The detected attenuated radiation may be output as attenuation values from the detector, and the attenuation values may be plotted as a sinogram. A computed tomography (CT) image may be reconstructed from a single X-ray source sinogram. As discussed below, by producing a single X-ray source sinogram from detector data that is collected from multiple traveling X-ray spots, the system may operate with two or more X-ray sources being constantly ON rather than turning the X-ray sources ON and OFF.

The traveling X-ray spot may be any positionable X-ray source that moves relative to the object to be scanned. The X-ray spot may be, for example, an X-ray beam, an X-ray source, or a pulse of X-ray energy. For example and referring to FIG. 1A, the traveling X-ray spot may be an X-ray beam that moves relative to a first scan track 110 by sequentially and separately exciting sample points $P_1$ through $P_N$ that are arranged along the first scan track 110 with an electron beam. The sample points $P_1$ through $P_N$ may be made from a material that emits X-rays when illuminated with the electron beam. Thus, a traveling X-ray spot may be created by moving the electron beam along the a first scan track 110.

In some systems, data from one traveling X-ray spot is used to reconstruct a computed tomography (CT) image. Such systems often include two X-ray beams that consecutively scan the object from different perspectives (e.g., a first X-ray beam scans the object from one side of the object and then a second X-ray beam separately scans the object from the opposite side). In systems that include two X-ray beams that scan consecutively, the electron gun that drives the X-ray tubes to produce X-rays is turned ON and OFF so that only one X-ray is on at a time. In such systems, the two X-ray tubes are generally turned ON and OFF rapidly so that only a single traveling X-ray spot illuminates the scanned object at a given time. Turning the X-rays ON and OFF rapidly may result in the need to use an electron gun with a more complex configuration than would be necessary if the electron beam could remain ON. For example, a configuration that uses more than one X-ray tube may require a power supply and electronics for each tube as well as electronics to switch the X-ray beams ON and OFF. Thus, a system in which the X-ray beams remain ON rather than switching ON and OFF such that the CT image is reconstructed from data collected from more than one traveling X-ray spot may be cheaper and easier to build and operate as compared to a system in which the X-ray beam is switched ON and OFF. In addition each tube is utilized 100% of the time instead of a fraction of the time, thus allowing for a faster scan or a lower X-ray flux in each X-ray tube.

Referring to FIG. 1A, a system 100 for producing a single X-ray source sinogram from detector data collected from multiple traveling X-ray spots is shown. The system 100 includes a first scan track 110, a second scan track 112, and a detector 115. The first scan track 110 and the second scan track 112 each include sample points (which also may be referred to as targets, emission targets, or sample spots) 0 to N. In the example shown in FIG. 1A, the first scan track 110 is the scan track "P" and the second scan track 112 is the scan track "R." The sample points 0 to N on the first scan track 110 are sample points $P_0$ to $P_N$, and the sample points 0 to N on the second track 112 are sample points $R_0$ to $R_N$. The sample points 0 to N may be made from a material that emits X-ray radiation when illuminated with radiation from a source (not shown). For example, the sample points 0 to N may be made from tungsten and the source may be an electron beam.

In system 100, the source may be placed above the tracks 110 and 112. For example, the source may be placed such that the radiation from the source travels into the page towards the tracks 110 and 112. The source may be scanned along the first scan track 110 by, for example, steering the radiation from the source with magnets (e.g., when the source is an electron beam) or by moving the source such that the radiation emitted from the sample points moves along the first scan track 110 to create a traveling X-ray spot. Similarly, the source may be scanned along the second scan track 112. The source may produce, for example, an electron beam or a laser of sufficient energy to excite one of the points 0 to N, or the source itself may produce an X-ray beam. In some implementations, the sample points 0 to N may be X-ray tubes, photocathodes, and/or field emission cathodes that emit X-rays in response to excitation. Regardless of the implementation of the sample points $P_0$ to $P_N$, and $R_0$ to $R_N$, each of the sample points $P_0$ to $P_N$ and $R_0$ to $R_N$ emits an X-ray spot in response to some excitation. Due to the arrangement of the sample points $P_0$ to $P_N$ along the first scan track 110, and $R_0$ to $R_N$ along the second scan track 112, selectively controlling the emission of X-rays from particular ones of the sample points $P_0$ to $P_N$ and $R_0$ to $R_N$ creates a traveling X-ray spot.

The first scan track 110 and the second scan track 112 also include blank spots (which also may be referred to as dark spots, blank targets, or blank samples) 125a, 125b, 125c, and 125d. The blank spots 125a, 125b, 125c, and 125d may be made from a material that does not emit X-rays when illuminated with radiation. In some implementations, the blank spots 125a, 125b, 125c, and 125d may emit X-rays when illuminated or otherwise excited, but the emitted X-rays are prevented from reaching the detector 115 by a X-ray blocking material such as lead.

In greater detail, in the example shown in FIG. 1A, at a given time, two moving X-ray spots, such as and $P_1$ and $R_1$ pass through the object 127 and are sensed by the detector 115. As discussed above, an X-ray spot is created when X-rays are emitted from one of the sample spots 0 to N. Referring to the example shown in FIG. 1A, a first X-ray spot moves along the first scan track 110 in an X-ray scan direction 130. Similarly, a second X-ray spot moves along the second scan track 112 in a second X-ray scan direction 140. When the first X-ray spot advances on the first scan track 110, for example, from $P_1$ to $P_2$, the second X-ray spot advances on the second scan track 112 by the same amount on the second scan track 112, for example, from $R_1$ to $R_2$. When the first and second X-ray spots reach the end of the track (e.g., $P_N$ and $R_N$), the X-ray spots retrace back from sample point "$P_N$" to sample point "$P_0$", and "$R_N$" to "$R_0$" along a retrace direction 135 and a retrace direction 145, respectively. Thus, the first and second X-ray spots move about the object 127 in a predictable manner.

The first and second X-ray spots pass through the object 127 and are sensed by the detector 115 as two attenuated X-ray spots, which may be referred to as "P" and "R," respectively. Thus, the sum of the energy in the first and second X-ray spots is sensed at the detector 115, and the detector 115 produces corresponding signal "S."

The signal at the detector 115 corresponding to a sample point "i" on the first scan track 110 can be expressed as shown in Equation (1):

$$s_i = \begin{cases} P_i + R_{i+1} & \text{for } 0 \leq i \leq N-1 \\ P_i + R_{2N-i-1} & \text{for } i = N \\ P_{2n-t} + R_{2N-i-1} & \text{for } N+1 \leq i \leq 2N-1 \\ P_{2N-i} + R_{i+1-2N} & \text{for } i = 2N \end{cases} \quad \text{Equation (1)}$$

The signals sensed at the detector corresponding to the X-ray spots emitted from $P_0$, $P_N$, $R_0$, and $R_N$ (e.g., the signals at the ends of the first and second scan tracks in the example shown in FIG. 1A) are all equal to zero or nearly zero. These signals are zero, or nearly zero, because little to no X-ray energy is produced at the blank spots 125a, 125b, 125c, and 125d. The blank spots 125a, 125b, 125c, and 125d may result from shadowing the X-ray beam at these sample points from the detector by a lead collimator or other X-ray blocking material. In some implementations, the blank spots 125a, 125b, 125c, and 125d may be made from materials that do not produce X-rays. Based on these signals being zero, the signals $P_i$ and $R_i$ corresponding to an X-ray spot emitted from an sample spot "i" are calculated as shown in Equation (2):

$$R_{i=odd} = \sum_{0 \le 2j \le i} S_{2j} - \sum_{2 \le 2j \le i} S_{2N-2j}$$

$$R_{i=even} = \sum_{1 \le 2j+1 \le i} (S_{2i+1} - S_{2N-2j-1})$$

$$P_{i=even} = \sum_{2 \le 2j \le i} S_{2N-2j} - \sum_{0 \le 2j \le i-2} S_{2j}$$

$$P_{i=odd} = \sum_{1 \le 2j+1 \le i} S_{2N-2j-1} - \sum_{1 \le 2j+1 \le i-2} S_{2j+1}$$

Equation (2)

where i=1 ... N corresponds to the sample spots on the first and second scan tracks 110, 112.

Accordingly, a sinogram may be calculated as if the X-ray spot originated from the first scan track 110 and the second scan track 112 separately even though the X-ray spots originate from both the first scan track 110 and the second scan track 112 simultaneously and illuminate the object 127 simultaneously. Thus, both the X-ray spots from the first scan track 110 and the second scan track 112 may remain ON rather than being switched ON and OFF. In contrast, in a system in which the X-ray spot originated from the first scan track 110 and then the second scan track 112, a sample spot on the first scan track 110 creates a first X-ray spot, and this X-ray spot is sensed by the detector 115 while the second scan track 112 is not producing an X-ray spot. However, in the technique discussed above and shown in Equations (1) and (2), both the first and second X-ray spots are produced at all times rather than being switched ON and OFF. Refraining from switching the first and second X-ray spots ON and OFF may allow the current used to generate the X-rays to be reduced by a factor of two and/or allow the scan speed to be increased. Additionally, by not switching the X-ray ON and OFF, instabilities caused by, for example, motion of the X-ray beam resulting from the beam being turned ON and OFF may be reduced. Reducing such instabilities may lead to higher-quality images by reducing image artifacts.

Figure 1B:
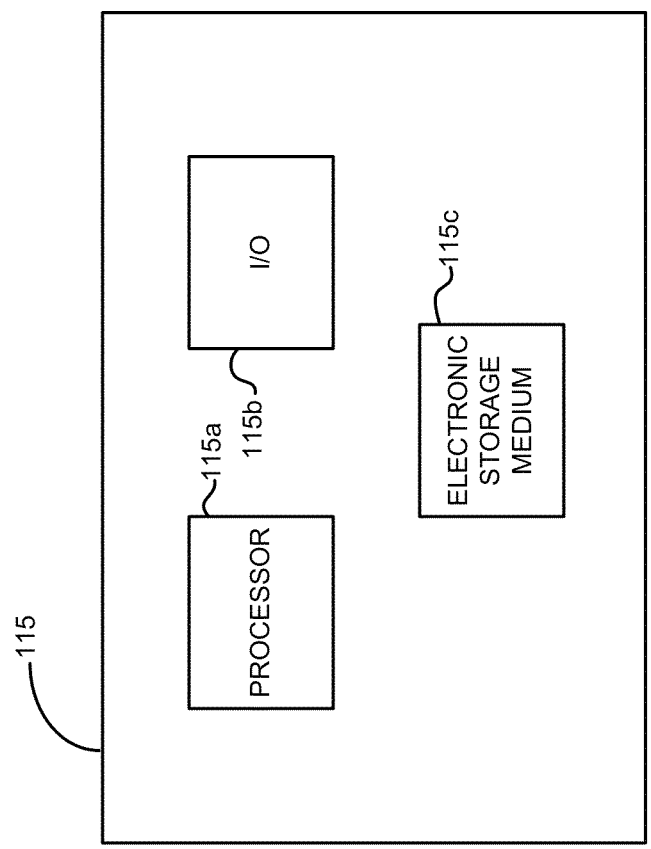
FIG. 1B shows a block diagram of electronics for a system such as the system of FIG. 1A.

Referring to FIG. 1B, the screening system 100 may also include a processor 115a, an input/output device 115b, and an electronic storage medium 115c, which in some implementations may be included in the detector 115. In some implementations, the processor 115a and electronic storage medium 115c may be included in a computer that is separate from the detector 115 and in communication with the detector 115. The electronic storage medium 115c stores instructions that, when executed by the processor 115a, cause the processor 115a to perform operations such as discussed above. The electronic storage 115c also may store data sensed by the detector 115 and instructions for retrieving the data from the detector 115. The electronic storage 115c may be any type of computer-readable medium. The processor 115a may be a processor suitable for the execution of a computer program such as a general or special purpose microprocessor, and any one or more processors of any kind of digital computer. Generally, a processor receives instructions and data from a read-only memory or a random access memory or both. In some implementations, the system 100 includes more than one processor 115a. The input/output device 115b may be any device able to transmit data to, and receive data from, the detector 115. For example, the input/output device 115b may be a mouse, a touch screen, a stylus, a keyboard, or any other device that enables a user to interact with the detector 115. In some implementations, the input/output device 115b may be an interface configured to couple the detector 115 to an external device such that the detector 115 may transfer data to the external device.

Figure 2:
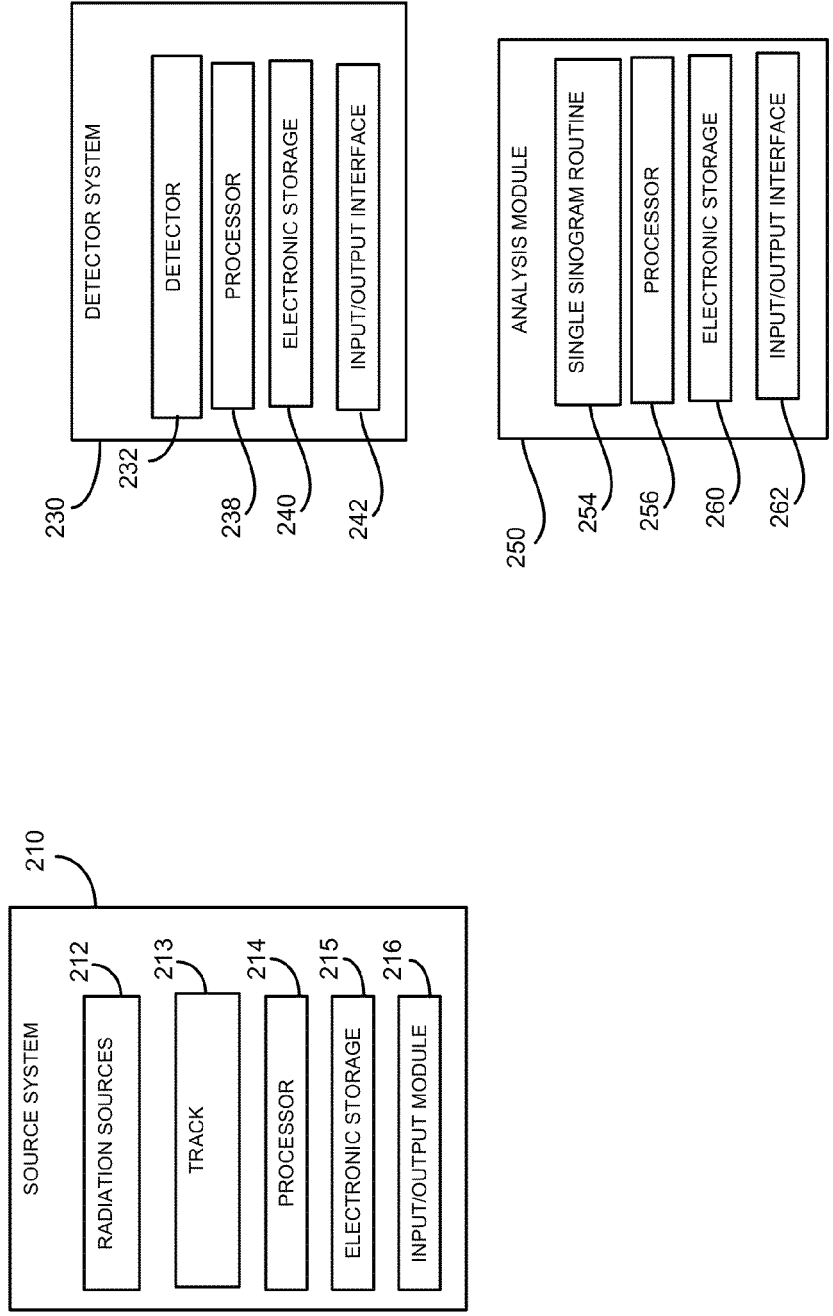
FIG. 2 shows a block diagram of an example system for producing an image of an object using detector data collected from multiple traveling X-ray spots.

Referring to FIG. 2, a block diagram of a system for producing a single X-ray source sinogram from detector data produced by detecting multiple traveling X-ray spots is shown. The system 200 may be similar to the system 100 discussed above with respect to FIG. 1A. The system 200 includes a source system 210, a detector system 230, and an analysis module 250.

The source system 210 includes multiple radiation sources 212, a track 213, a processor 214, electronic storage 215, and an input/output interface 216. The multiple radiation sources 212 produce multiple beams that move relative to an object and/or a detector in a predictable manner or a known pattern. The multiple beams move relative to the object concurrently, simultaneously, or otherwise operate at the same time to scan the object. The multiple radiation sources 212 may be sources that produce multiple moving X-ray spots, as discussed above with respect to FIG. 1A.

The source system 210 also includes the track 213. The track 213 may be similar to the scan tracks 110 and 112 discussed above with respect to FIG. 1A. The track 213 may include multiple tracks (such as the tracks 110 and 112 shown in FIG. 1A), and each of the multiple tracks has a configuration. A configuration of a track may be a shape of the track, a size of the track, and/or a placement of targets along the track. As shown in FIG. 1A, the tracks 110 and 112 have a curved shape, however, in other examples, the track 213 may be rectilinear. The tracks may have different configurations. For example, in a system that includes two tracks, one track may have a rectilinear shape and the other track may have a curved shape. The track 213 may also include dark spots or blank targets located at either end of the track 213. The dark spots or blank targets do not emit X-rays, or suppress the emission of X-rays. In other implementations, the dark spots or blank targets may suppress X-ray emissions by placing an X-ray blocking material such as lead between the path of a target and the object. The track 213 may be configured to be placed into an existing non-rotating CT system.

The system 200 also includes a detector system 230 that includes a detector 232, a processor 238, an electronic storage 240, and an input/output interface 242. The detector 232 is made from a material that produces a signal, or other representation, in response to interacting with the radiation from the radiation sources 212. The signal may be, for example, an electronic signal or an optical signal. The amplitude of the signal may be proportional to the amount of radiation detected by the detector. The detector 232 may be an array of thousands of detectors (e.g., 30,000 detectors). In some implementations, the detector system 230 includes a processor 238 and an electronic storage 240. The processor 230 receives signals from an active area of the detector 232 and may convert the signals into an electronic signal suitable for additional processing and analysis. The detector system 230 also includes an input/output interface 242 that allows signals and other outputs from the detector to be coupled out of the detector 232 for further analysis and processing.

The system 200 also includes an analysis module 250 that includes a single source sinogram routine 254, a processor 256, an electronic storage 260, and an input/output interface 262. The single source sinogram routine 254 may be used to analyze data from the detector 232 using Equations 1 and 2 to determine a signal at the detector 232 that corresponds to a particular position along the track 213. The electronic storage 260 stores the outputs of the routine 254. The input/output interface 262 may include tactile devices that allow a user to access and manipulate data stored in the electronic storage 260. The input/output interface 262 also may include a visual display that allows a single source sinogram, or other image generated by the routine 254, to be visually presented to a user of the system 200.

The electronic storage components 215, 240, and 260 may be volatile memory, such as RAM. In some implementations, and the electronic storage components 215, 240, and 260 may include both non-volatile and volatile portions or components. The processors 214, 238, and 256 may be processors suitable for the execution of a computer program such as a general or special purpose microprocessor, and any one or more processors of any kind of digital computer. Generally, a processor receives instructions and data from a read-only memory or a random access memory or both.

Figure 3:
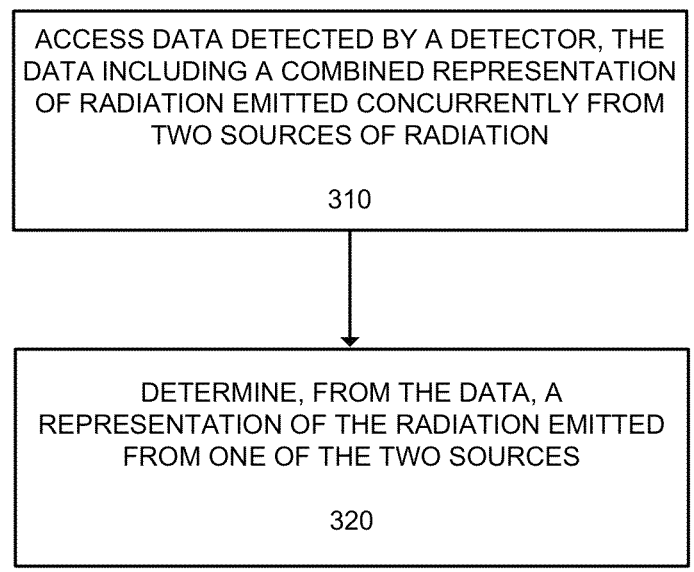
FIG. 3 shows an example process for reconstructing a signal from multiple sources.

Referring to FIG. 3, an example process for reconstructing a signal from multiple radiation sources is shown. The process 300 may be performed by one or more processors included in the system 100 or the system 200.

Data detected by a detector is accessed (310). The data includes a combined representation of radiation emitted concurrently from two or more sources of radiation. The combined representation of radiation may be a numerical value that represents the sum of the intensities of the radiation from the two or more sources of radiation. The detector may collect radiation from X-rays transmitted through the object, coherently scattered by the object or backscattered by the object under inspection. The two or more sources of radiation may be two traveling X-ray spots similar to those discussed with respect to FIG. 1A. However, the two or more sources of radiation may be any sources of radiation that move relative to an object (such as the object 127) and a detector (such as the detector 115) in a predictable manner A representation of the radiation emitted from one of the sources of radiation is determined from the data (320). The representation may be determined using the techniques shown in Equations 1 and 2, and the representation may be a signal at the detector that is attributable to one of the sources of radiation. In some implementations, the representation may include one or both of the position of the source of radiation relative to the detector and a view angle of the sources of radiation.

In the example shown in FIG. 1A, two traveling X-ray spots (e.g., an X-ray spot from the first scan track 110 and an X-ray spot from the second scan track 112) scan the object 127. However, in some implementations, more than two X-ray spots may be used. By increasing the number of blank spots, the techniques discussed above are applicable to implementations that use more than two X-ray spots. The number of blank spots (such as the blank spots 125a, 125b, 125c, and 125d) is proportional to the number of X-ray spots as 2n(n−1), where "n" is the number of moving X-ray spots.

Figure 4:
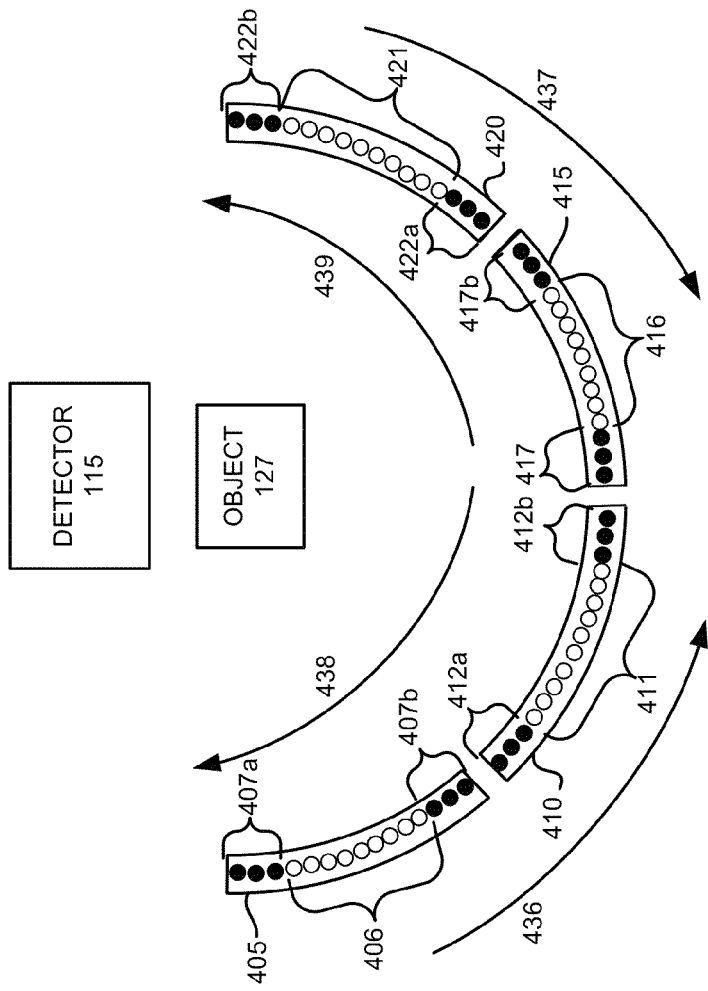
FIG. 4 shows another example system for producing a single X-ray source sinogram from detector data collected from multiple traveling X-ray spots.

Referring to FIG. 4, an imaging system 400 for producing a single X-ray source sinogram from detector data collected from multiple traveling X-ray spots is shown. The system 400 includes four scan tracks, a scan track "P" 405, a scan track "U" 410, a scan track "T" 415, and a scan track "R" 420. Each of the scan tracks 405, 410, 415, and 420 include sample spots 406, 411, 416, and 421, respectively, that include discrete emission targets that emit x-rays in response to interaction with radiation from a source (not shown) or other excitation. The sample spots 406, 411, 416, and 421 that are respectively included with the scan tracks 405, 410, 415, and 420 may be similar to the sample spots discussed above with respect to FIG. 1A. The system 400 also includes twenty-four total blank spots, with six blank spots included in each scan track (three at either end of each track). The scan track 405 includes blank spots 407a and 407b, the scan track 410 includes blank spots 412a and 412b, the scan track 415 includes blank spots 417a and 417b, and the scan track 420 includes blank spots 422a and 422b. Each of the blank spots 407a, 407b, 412a, 412b, 417a, 417b, 422a, and 422b include three discrete blank spots as shown in FIG. 4.

The imaging system 400 concurrently scans the object 127 with four X-ray beams (not shown), with one X-ray beam emerging from each of the scan tracks 405, 410, 415, and 420. The four X-ray beams, which may be considered to be traveling X-ray spots, move relative to the object 127. The four traveling X-ray spots move relative to the object 127 by sequentially and separately exciting the emission targets included in the sample spots 406, 411, 416, and 421 in each of the scan tracks 405, 410, 415, and 420. As discussed above, the emission targets of the sample spots 406, 411, 416, and 421 emit X-ray radiation when excited. Thus, sequentially and separately exciting the sample spots 406, 411, 416, and 421 results in one traveling X-ray spot for each of the four scan tracks 405, 410, 415, and 420 such that a total of four traveling X-ray spots that concurrently scan the object 127.

In operation, the sample spots 406 and 411 and the sample spots 416 and 421 are sequentially and separately excited in scan directions 436 and 437, respectively, and retraced along scan directions 438 and 439, respectively. For the initial scan-retrace, the signal at the detector 115 may be expressed as shown in Equations (3) and (4):

$$S_i = P_i + R_{i+1} + T_{i+2} + U_{i+3}, \quad \text{Equation (3)}$$

where P, R, T, and U are, respectively, the scan tracks 405, 410, 415, and 420 and i=0 to N.

On the second scan-retrace, the order is $$S_i = R_i + P_{i+1} + U_{i+2} + T_{i+3}. \quad \text{Equation (4)}$$

When done in this order, and taking into account the six blank spots present on each scan track, the contributions to the sinogram from each X-ray spot may be determined using Equations 1 and 2 discussed above. The scanning electron beam or other source of excitation for the emission targets has a variable scan speed capability at the end of each scan track such that the scan speed can be increased or decreased to allow for a scan permutation (e.g., a change in the order of scanning of the emission targets).

Figure 5:
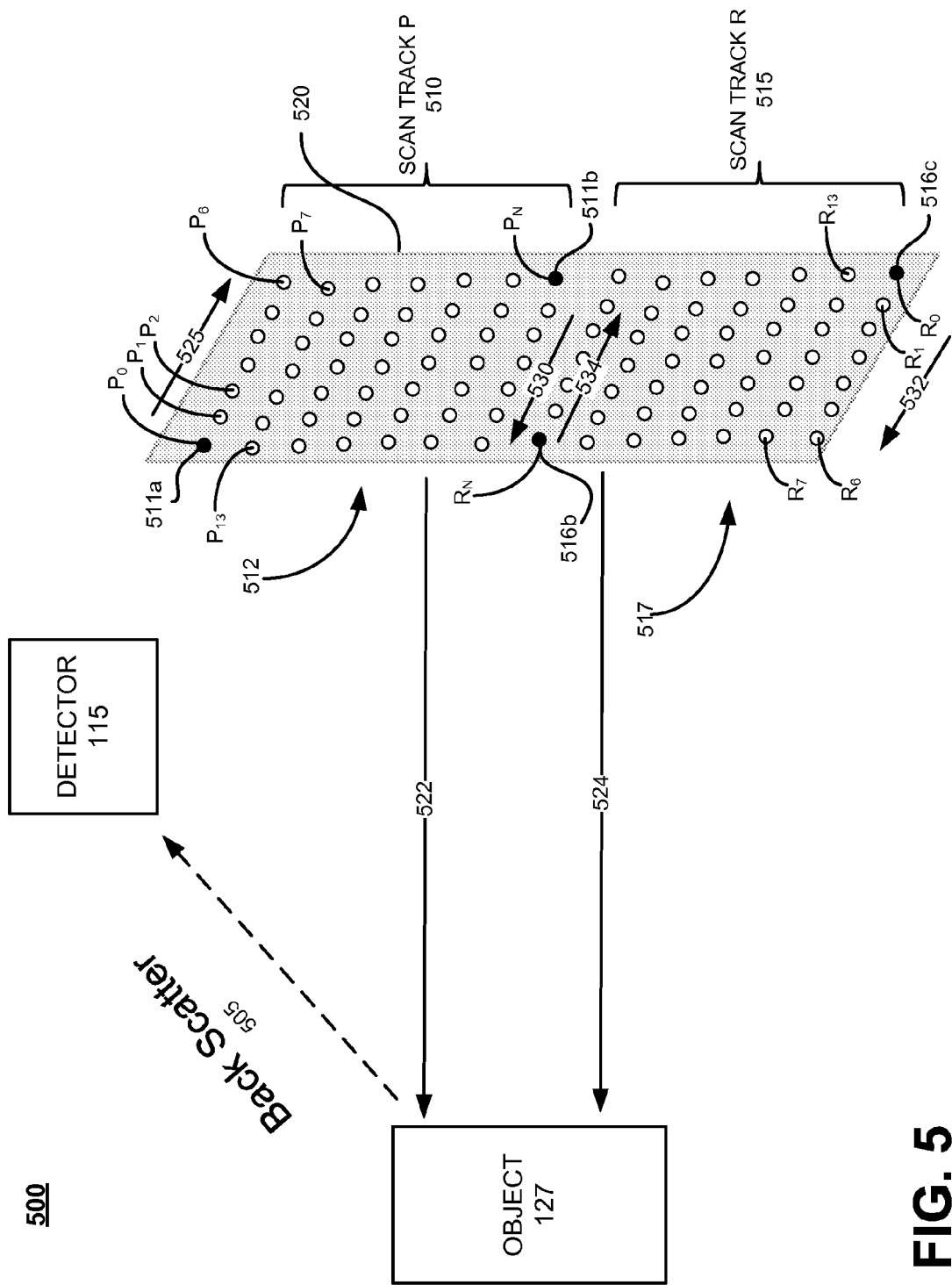
FIG. 5. shows an example system for producing a single X-ray source sinogram from detector data representing back scatter of multiple traveling X-ray spots from an object.

Referring to FIG. 5, an imaging system for producing a single X-ray source sinogram from multiple traveling X-ray spots is shown. In the system 500, the object 127 is concurrently scanned with X-ray spots 522 and 524. The detector 115 detects radiation 505 that is backscattered from the object 127 as a result of the object 127 being scanned by the X-ray spots 522 and 524.

The system 500 includes a scan track "P" 510 and a scan track "R" 515, both of which are formed on a surface 520. Each of the scan tracks 510 and 515 include two blank spots 511a, 511b and 516a, 516b, respectively. Each of the scan tracks 510 and 515 include multiple sample spots 512 and 517 that each include discrete emission targets. The emission targets of the sample spots 512 and 517 are arranged in a two-dimensional pattern on the surface 520. Each of the sample spots 512 and 517 emit X-rays when illuminated with radiation or otherwise excited. Thus, separately and sequentially exciting the sample spots 512 and 517 creates the two moving X-ray spots 522 and 524, with the X-ray spot 522 being emitted from the scan track 510 and the X-ray spot 524 being emitted from the scan track 515.

Each of the two moving X-ray spots 522 and 524 travels in a horizontal zigzag direction relative to the surface 520. The X-ray spot 522 begins at $P_0$ (which corresponds to the blank spot 511a), moves to $P_1$ along a scan direction 525, and eventually moves to $P_6$. After $P_6$, the X-ray spot moves to $P_7$ and then to $P_{13}$. The initial scan ends at $P_N$ (which corresponds to the blank spot 511b). The retrace scan begins at $P_N$ and retraces along a retrace direction 530 in the opposite direction of the initial scan to return to $P_0$. Similarly, the X-ray spot 524 begins at $R_0$ and moves along a scan direction 532 to the position $R_6$ and then $R_7$, ending at $R_N$. The X-ray spot 524 is retraced along a retrace direction 534 to return to $R_0$.

The first and second X-ray spots move about the object 127 in a predictable manner. For example, when the first X-ray spot 522 advances on the scan track 510, for example, from $P_i$ to $P_2$, the X-ray spot 524 advances on the scan track 515 by the same amount, for example, from $R_1$ to $R_2$. Thus, the analysis shown in Equations 1 and 2 may be applied to the back scatter detected at the detector 115 to determine a representation of back scatter attributable to the X-ray spot 522 separate from the back scatter attributable to the X-ray spot 524.

The blank spots 511a, 511b, 516a, and 516b may be made from a material that does not emit X-rays, or emits a negligible amount of X-rays, when illuminated with radiation or otherwise excited. In some implementations, the blank spots 511a, 511b, 516a, and 516b emit X-rays when illuminated or otherwise excited, but the emitted X-rays are prevented from reaching the object 127 (and thus are not scattered to the detector 115 for detection) by a X-ray blocking material such as lead placed between the surface 520 and the object 127.

Other implementations are within the scope of the following claims. For example, although FIG. 1A shows a system 100 with one detector 115, in some implementations more than one detector may be used. In these implementations, the techniques discussed above may be performed for each detector. In some implementations, many thousands of detectors (e.g., 30,000 detectors) may be included. In some implementations, the first and second scan tracks 110, 112 shown in FIG. 1A may have a flat surface. The first and second scan tracks 110, 112 may be formed on a unitary surface. The sample spots may be equally spaced with respect to each other along the scan tracks or the sample spots may be placed in an arrangement in which the sample spots are arranged other than being equally spaced with respect to each other. In each of the scan tracks 110, 112, 405, 410, 415, 420, 510, and 515 discussed above additional emission targets may be included, however, scan tracks used in a particular system include the same number of discrete emission targets.

Referring to FIG. 5, the X-ray spots 522 and 524 may be scanned along a vertical zigzag direction such that the X-ray spot 522 initially moves from $P_0$ to $P_{13}$, and the X-ray spot 524 initially moves from $R_0$ to $R_{13}$. The emission targets that are included in the X-ray spots 522 and 524 may be scanned by the source or otherwise excited in any sequential order so long as the same order (in reverse) is repeated on the retrace scan. For example, the emission targets may be scanned in a spiral sequence. In some implementations, the X-ray spots 522 and 524 may be scanned along in another manner, for example, the emission targets included in the scan tracks 510 and 515 may be excited in a pre-defined and non-linear manner, such as in a spiral pattern.

What is claimed is:

1. An imaging system comprising:
    a first source of radiation configured to direct first radiation towards an object by moving in a predetermined path along a first set of targets, the first set of targets including: (i) multiple emission targets placed at different positions and configured to emit first radiation in response to being irradiated with the first source, and (ii) multiple blank targets placed at different positions and configured to suppress the emission of the first radiation in response to being irradiated with the first source;
    a second source of radiation configured to direct second radiation towards the object concurrently with the first radiation by moving in a predetermined path along a second set of targets, the second set of targets including: (i) multiple emission targets placed at different positions and configured to emit second radiation in response to being irradiated with the second source, and (ii) multiple blank targets placed at different positions and configured to suppress the emission of the second radiation in response to being irradiated with the second source;
    a detector configured to detect the first radiation and the second radiation and to create sets of data, each set of data comprising a representation of a detected combined radiation of a combination of the first radiation emitted at a particular target of the first track with the second radiation emitted at a particular target of the second track;
    a processor; and
    an electronic storage coupled to the processor, the electronic storage including instructions that, when executed, cause the processor to:
        receive the sets of data from the detector, and
        determine, from the sets of data, a representation of the radiation emitted from a particular target of the first set of targets based on the representations of detected combined radiation and the placement of at least one of the blank targets in at least one of the predetermined paths.

2. A computer-implemented method of reconstructing a signal from multiple radiation sources, the method comprising:
    accessing, using a processor, sets of data detected by a detector, each set of data comprising a representation of detected combined radiation emitted concurrently from:
        a particular target of a first set of targets, the first set of targets including: (i) multiple emission targets placed at different positions and configured to emit first radiation in response to being irradiated with a first source that moves in a predetermined path along the first set of targets, and (ii) multiple blank targets placed at different positions and configured to suppress the emission of the first radiation in response to being irradiated with the first source; and
        a particular target of a second set of targets, the second set of targets including: (i) multiple emission targets placed at different positions and configured to emit second radiation in response to being irradiated with a second source that moves in a predetermined path along the second set of targets, and (ii) multiple blank targets placed at different positions and configured to suppress the emission of the second radiation in response to being irradiated with the second source; and
    determining using the processor, from the sets of data, a representation of the radiation emitted from a particular target of the first set of targets based on the representations of detected combined radiation and the placement of at least one of the blank targets in at least one of the predetermined paths.

3. A non-transitory computer-readable medium encoded with a computer program comprising instructions that, when executed, operate to cause a computer to perform operations comprising:
  accessing sets of data detected by a detector, each set of data comprising a representation of detected combined radiation emitted concurrently from:
    a particular target of a first set of targets, the first set of targets including: (i) multiple emission targets placed at different positions and configured to emit first radiation in response to being irradiated with a first source that moves in a predetermined path along the first set of targets, and (ii) multiple blank targets placed at different positions and configured to suppress the emission of the first radiation in response to being irradiated with the first source; and
    a particular target of a second set of targets, the second set of targets including: (i) multiple emission targets placed at different positions and configured to emit second radiation in response to being irradiated with a second source that moves in a predetermined path along the second set of targets, and (ii) multiple blank targets placed at different positions and configured to suppress the emission of the second radiation in response to being irradiated with the second source; and
  determining from the sets of data, a representation of the radiation emitted from a particular target of the first set of targets based on the representations of detected combined radiation and the placement of at least one of the blank targets in at least one of the predetermined paths.

4. The system of claim 1, wherein determine, from the sets of data, a representation of the radiation emitted from a particular target of the first set of targets comprises:
  determine relative positions of all emission targets on all sets of targets with respect to each other and with respect to the blank targets for each set of targets;
  determine data sets that the representation of the radiation emitted from the particular target can be determined from; and
  determine individual contributions of all individual emission targets in all sets of targets from the determined data sets using the determined relative positions with respect to each other and with respect to the blank targets for each set of targets.

5. The system of claim 4, wherein the predetermined paths of the sources along the sets of targets and the placement of the blank targets encode information into the data sets which allows the determination of the individual contributions of the individual emission targets using a predetermined set of algebraic relationships.

6. The system of claim 1, wherein the processor determines the representation of the radiation emitted from a particular target of the first set of targets based on the placement of one or more additional blank targets in one or more additional sets of targets.

7. The system of claim 1, wherein the sources comprise electron beams or other sources that create (i) multiple x-rays sources moving in the predetermined paths and (ii) blank spots.

8. The system of claim 1, wherein each set of targets is placed on a corresponding track.

9. The system of claim 1, wherein the first source and the second source move concurrently relative to the object.

10. The system of claim 1, wherein the representation of detected combination radiation comprises a summation of an intensity of the first radiation and an intensity of the second radiation after the first and second radiation interact with the object.

11. The system of claim 1, wherein the first and second radiation pass through the object, the object attenuates the first radiation and the second radiation, and
  wherein the representation of detected combined radiation comprises the attenuated first radiation and the attenuated second radiation.

12. The method of claim 2, wherein determining using the processor, from the sets of data, a representation of the radiation emitted from a particular target of the first set of targets comprises:
  determining relative positions of all emission targets on all sets of targets with respect to each other and with respect to the blank targets for each set of targets;
  determining data sets that the representation of the radiation emitted from the particular target can be determined from; and
  determining individual contributions of all individual emission targets in all sets of targets from the determined data sets using the determined relative positions with respect to each other and with respect to the blank targets for each set of targets.

13. The method of claim 12, wherein the predetermined paths of the sources along the sets of targets and the placement of the blank targets encode information into the data sets which allows the determination of the individual contributions of the individual emission targets using a predetermined set of algebraic relationships.

14. The method of claim 2, wherein determining using the processor, from the sets of data, a representation of the radiation emitted from a particular target of the first set of targets is further based on the placement of one or more additional blank targets in one or more additional sets of targets.

15. The method of claim 2, wherein the sources comprise electron beams or other sources that create (i) multiple x-rays sources moving in the predetermined paths and (ii) blank spots.

16. The method of claim 2, wherein each set of targets is placed on a corresponding track.

17. The method of claim 2, wherein the first source and the second source move concurrently relative to the object.

18. The method of claim 2, wherein the representation of detected combination radiation comprises a summation of an intensity of the first radiation and an intensity of the second radiation after the first and second radiation interact with the object.

19. The method of claim 2, wherein the first and second radiation pass through the object, the object attenuates the first radiation and the second radiation, and
  wherein the representation of detected combined radiation comprises the attenuated first radiation and the attenuated second radiation.

* * * * *